US012324789B2

(12) United States Patent
Changoer et al.

(10) Patent No.: US 12,324,789 B2
(45) Date of Patent: Jun. 10, 2025

(54) METHOD TO TREAT PSORIASIS

(71) Applicant: APIRx Pharmaceutical USA, LLC, New York, NY (US)

(72) Inventors: Lekhram Changoer, Ridderkerk (NL); George Anastassov, New York, NY (US)

(73) Assignee: APIRx Pharmaceutical USA, LLC, New York, NY (US)

( * ) Notice: Subject to any disclaimer, the term of this patent is extended or adjusted under 35 U.S.C. 154(b) by 0 days.

(21) Appl. No.: 16/106,420

(22) Filed: Aug. 21, 2018

(65) Prior Publication Data
US 2019/0060250 A1 Feb. 28, 2019

Related U.S. Application Data

(60) Provisional application No. 62/550,877, filed on Aug. 28, 2017.

(51) Int. Cl.
*A61K 31/05* (2006.01)
*A61K 9/00* (2006.01)
*A61K 31/352* (2006.01)
*A61K 47/12* (2006.01)
*A61K 47/36* (2006.01)
*A61K 47/46* (2006.01)
*A61P 17/06* (2006.01)

(52) U.S. Cl.
CPC ............ *A61K 31/05* (2013.01); *A61K 9/0014* (2013.01); *A61K 31/352* (2013.01); *A61K 47/12* (2013.01); *A61K 47/36* (2013.01); *A61K 47/46* (2013.01); *A61P 17/06* (2018.01)

(58) Field of Classification Search
None
See application file for complete search history.

(56) References Cited

U.S. PATENT DOCUMENTS

| 8,808,734 | B2 * | 8/2014 | Winnicki | A61K 45/06 424/450 |
| 2008/0255224 | A1 * | 10/2008 | Blum | A61P 17/06 514/454 |
| 2016/0235661 | A1 | 8/2016 | Changoer et al. | |
| 2017/0112855 | A1 * | 4/2017 | Modi | A61K 9/06 |

FOREIGN PATENT DOCUMENTS

| GB | 2542797 A | 5/2017 | |
| WO | WO-2014082609 A1 * | 6/2014 | ......... A61K 47/6907 |
| WO | WO-2016103254 A1 * | 6/2016 | ............ A61K 47/06 |
| WO | WO2016209802 A1 | 12/2016 | |
| WO | WO2017027553 A1 | 2/2017 | |

OTHER PUBLICATIONS

Smejkalova et al. "Topical Drug Delivery by Hyaluronan Polymeric Micelles". Front. Bioeng. Biotechnol. Conference Abstract: 10th World Biomaterials Congress. Published Online Mar. 30, 2016. (Year: 2016).*

Kim, J.S., et al. "Cannabinoid receptors: Their impact in epidermal differentiation and possible role in treatment of psoriasis", J. Am. Acad. Derm., AB 28, p. 1097, May 2015.

Wilkinson, J.D. et al. "Cannabinoids inhibit human keratinocyte proliferation through a non-CB1/CB2 mechanism and have a potential therapeutic value in the treatment of psoriasis", J. Derm. Sci. (2007) 45, 87-92.

Ando T, Xiao W, Gao P, Namiranian S, Matsumoto K, Tomimori Y, et al. Critical Role for Mast Cell Stat5 Activity in Skin Inflammation. Cell Reports. 6 (2):366-76.

Biro T, Toth B I, Hasko G, Paus R, Pacher P. The Endocannabinoid System of the Skin in Health and Disease: Novel Perspectives and Therapeutic Opportunities. Trends in Pharmacological Sciences. 2009; 30 (8):411-20.

Borrelli F, Pagano E, Romano B, Panzera S, Maiello F, Coppola D, et al. Colon Carcinogenesis is Inhibited by the TRPM8 Antagonist Cannabigerol, a Cannabis-Derived Non-Psychotropic Cannabinoid. Carcinogenesis. 2014; 35 (12):2787-97.

Brenneisen R, Egli A, Elsohly M A, Henn V, Spiess Y. The Effect of Orally and Rectally Administered Delta 9-Tetrahydrocannabinol on Spasticity: a Pilot Study With 2 Patients. International Journal of Clinical Pharmacology and Therapeutics. 1996; 34 (10):446-52.

Campos A C, Moreira F, Gomes F V, Del Bel E A, Guimarães F S. Multiple Mechanisms Involved in the Large-Spectrum Therapeutic Potential of Cannabidiol in Psychiatric Disorders. Philosophical Transactions of the Royal Society of London Series B, Biological Sciences. 2012; 367 (1607):3364-78.

Cascio M, Gauson L, Stevenson L, Ross R, Pertwee R. Evidence that the Plant Cannabinoid Cannabigerol is a Highly Potent A(2)-Adrenoceptor Agonist and Moderately Potent 5HT(1A) Receptor Antagonist. Br. J. Pharmacol. 2010; 159 (1):129-41.

Cuba L F, Salum F G, Cherubini K, Figueiredo M A. Cannabidiol: An Alternative Therapeutic Agent for Oral Mucositis? Journal of Clinical Pharmacy and Therapeutics. 2017.

Guttman-Yassky E, Krueger J G, Lebwohl M G. Systemic Immune Mechanisms in Atopic Dermatitis and Psoriasis with Implications for Treatment. Experimental Dermatology. 2017.

Jäger A, Dardalhon V, Sobel R A, Bettelli E, Kuchroo V K. Th1, Th17 and Th9 Effector Cells Induce Experimental Autoimmune Encephalomyelitis with Different Pathological Phenotypes. Journal of Immunology (Baltimore, Md.: 1950). 2009; 183 (11):7169-77.

Jastrza, et al, "The Origin and Biomedical Relevance of Cannabigerol" Int. J. Mol. Sci. 2022, 23, 7929.

McGilveray I J. Pharmacokinetics of Cannabinoids. Pain Research & Management. 2005; 10 Suppl A:15a-22a.

Mechoulam R, Peters M, Murillo-Rodriguez E, Hanuš L O. Cannabidiol—Recent Advances. Chemistry & Biodiversity. 2007; 4 (8):1678-92.

NIAMS. Questions and Answers about Psoriasis: National Institute of Arthritis and Musculoskeletal and Skin Diseases (NIAMS); 2016 [updated Jul. 2016. Available from: https://www.niams.nih.gov. health_info/psoriasis/#5.

(Continued)

*Primary Examiner* — Leslie A. Royds Draper
(74) *Attorney, Agent, or Firm* — Knobbe, Martens, Olson & Bear, LLP

(57) ABSTRACT

A method to treat the skin condition psoriasis is described in this invention. The method comprises topical application of a composition containing cannabinoids, in particular cannabidiol and cannabigerol at a concentration of 3%-20% by weight of the composition. The topical application is applied at least twice daily for six weeks.

6 Claims, No Drawings

(56) References Cited

OTHER PUBLICATIONS

Raphael I, Nalawade S, Eagar T N, Forsthuber T G. T Cell Subsets and Their Signature Cytokines in Autoimmune and Inflammatory Diseases. Cytokine. 2015; 74 (1):5-17.

Ryberg E, Larsson N, Sjogren S, Hjorth S, Hermansson N, Leonova J, et al. The Orphan Receptor GPR55 is a Novel Cannabinoid Receptor. Br. J. Pharmacol. 2007; 152 (7):1092-101.

Small-Howard A L, Shimoda L M, Adra C N, Turner H. Anti-Inflammatory Potential of CB1-Mediated Camp Elevation in Mast Cells. The Biochemical Journal. 2005; 388 (Pt 2):465-73.

Toh M R, Teo V, Kwan Y H, Raaj S, Tan S Y, Tan J Z. Association Between Number of Doses Per Day, Number of Medications and Patient's Non-Compliance, and Frequency of Readmissions in a Multi-Ethnic Asian Population. Preventive Medicine Reports. 2014; 1:43-7.

Turcotte C, Blanchet M R, Laviolette M, Flamand N. The CB2 Receptor and Its Role as a Regulator of Inflammation. Cellular and Molecular Life Sciences: CMLS. 2016; 73 (23):4449-70.

Valdeolivas S, Navarrete C, Cantarero I, Bellido M L, Munoz E, Sagredo O. Neuroprotective Properties of Cannabigerol in Huntington's Disease: Studies In R6/2 Mice and 3-Nitropropionate-Lesioned Mice. Neurotherapeutics: The Journal of the American Society for Experimental Neuro Therapeutics. 2015; 12 (1):185-99.

WHO. Global Report on Psoriasis. World Health Organisation; 2016. p. 49.

Cheng Y, Hitchcock S A., Targeting Cannabinoid Agonists for Inflammatory and Neuropathic Pain. Expert Opinion on Investigational Drugs. 2007; 16 (7):951-65.

Indhumathi et al., T Helper-2 Cytokine/Regulatory T-Cell Gene Polymorphisms and Their Relation With Risk of Psoriasis in a South Indian Tamil Cohort. Human immunology. 2017; 78 (2):209-15.

Iseger T A, Bossong M G., A Systematic Review of the Antipsychotic Properties of Cannabidiol in Humans. Schizophrenia Research. 2015; 162 (1-3):153-61.

Lambert D M, Fowler C J., The Endocannabinoid System: Drug Targets, Lead Compounds, and Potential Therapeutic Applications. J. of Medicinal Chemical. 2005; 48 (16):5059-87.

Maccarrone et al., Endocannabinoid Signaling at the Periphery: 50 Years After THC. Trends in Pharmacological Sciences. 2015; 36 (5):277-96.

Mashiko et al., Human Mast Cells Are Major Il-22 Producers in Patients with Psoriasis and Atopic Dermatitis. The Journal of Allergy and Clinical Immunology. 2015; 136 (2):351-9.el.

Norooznezhad A H, Norooznezhad F., Cannabinoids: Possible Agents for Treatment of Psoriasis via Suppression of Angiogenesis and Inflammation. Med. Hypotheses. 2017; 99:15-8.

Russo E B et al., Agonistic Properties of Cannabidiol at 5-HT1a Receptors. Neurochemical Research. 2005; 30 (8):1037-43.

Sugawara et al., Endocannabinoids Limit Excessive Mast Cell Maturation and Activation in Human Skin. The Journal of Allergy and Clinical Immunology. 2012; 129 (3):726-38.e8.

Weiss L et al., Cannabidiol Lowers Incidence of Diabetes in Non-Obese Diabetic Mice. Autoimmunity. 2006; 39 (2): 143-51.

\* cited by examiner

METHOD TO TREAT PSORIASIS

CROSS-REFERENCE TO RELATED APPLICATIONS

This application claims the benefit of U.S. Provisional Application No. 62/550,877, filed Aug. 28, 2017. Each of the above-referenced patent applications is incorporated by reference in its entirety.

BACKGROUND OF THE INVENTION

Field of the Invention

This invention concerns the field of treatment for skin conditions caused by alterations in the immune system. Various skin conditions exist and various methods have been introduced for treatment.

In particular, this invention concerns a method to treat psoriasis using a topical composition for application on affected skin areas.

Description of the Related Technology

The cannabis plant has many naturally occurring substances that are of great interest in the fields of science and medicine. Isolated compounds from the cannabis plant include $\Delta^9$-tetrahydrocannabinol (THC), cannabidiol (CBD), cannabichromene (CBC), cannabigerol (CBG), cannabinol (CBN), cannabidivarin (CBDV), among other compounds. While THC has psychoactive effects, CBD, CBC, CBG, and CBDV do not. Isolated alkaloid compounds from the cannabis plant are called cannabinoids. There are a total of one hundred and forty one (141) cannabinoids that have been isolated from the cannabis plant. Many researchers have confirmed the medicinal value of cannabinoids. Cannabinoids have been investigated for possible treatment of seizures, nausea, vomiting, lack of appetite, pain, arthritis, inflammation, and other conditions.

Cannabinoids can be isolated by extraction or cold pressing from cannabis plants. Plants in the cannabis genus include *Cannabis sativa, Cannabis ruderalis*, and *Cannabis indica*. These plants are natural sources of cannabinoids. Cannabinoids are also available in synthetic forms. Methods to synthesize cannabinoids in lab settings were discovered and are still currently practiced. Synthetic cannabinoids are more targeted, in that the synthetic compound usually comes isolated without other cannabinoids and/or other compounds mixed in.

Nabilone (racemic(6aR,10aR)-1-hydroxy-6,6-dimethyl-3-(2-methyloctan-2-yl)-7,8,10,10a-tetrahydro-6H-benzo[c]chromen-9(6aH)-one), a synthetic cannabinoid, is believed to have fewer undesired side effects than THC. Nabilone mimics the chemical compound structure of THC. THC also exists in synthetic form under the name Dronabinol ((−)-(6aR,10aR)-6,6,9-trimythel-3-pentyl-6a,7,8,10a-tetrahydro-6H-benzo[c] chromen-1-ol)). The U.S. Food and Drug Administration approved nabilone and dronabinol for treatment of chemotherapy-induced nausea and vomiting and later for cachexia due to HIV/AIDS. In the United States, nabilone is marketed under the name Cesamet® and dronabinol under the name Marinol®. There are also generic versions of the drugs available on the market.

The IUPAC nomenclature of THC is (−)-(6aR,10aR)-6,6,9-trimethyl-3-pentyl-6a,7,8,10a-tetrahydro-6H-benzo[c]chromen-1-ol. CBD's IUPAC nomenclature is 2-((1S,6S)-3-methyl-6-(prop-1-en-2-yl)cyclo-hex-2-enyl)-5-pentylbenzene-1,3-diol). CBC has the IUPAC nomenclature of 2-methyl-2-(4-methylpent-3-enyl)-7pentyl-5-chromenol. CBG has the IUPAC nomenclature of 2-[(2E)-3,7-dimethylocta-2,6-dienyl]-5-pentyl-benzene-1,3-diol. These are among the most prominent alkaloid compounds in the family of compounds extracted from the cannabis plant referred to as cannabinoids.

Cannabidiol (CBD) is a major phytocannabinoid, accounting for up to 40% of the plant's extract. CBD is a CB-1 receptor antagonist, while THC is a CB-1 receptor agonist. A 2010 research found that cannabis strains with higher concentration of CBD did not produce the short-term memory impairment normally seen in high THC cannabis strains, a characteristic attributed to the CB-1 receptor antagonist nature of CBD. CBD is considered to have a wider scope of medical applications than THC.

Because it is a relatively unknown cannabinoid, cannabigerol (CBG) remains understudied and its effects are only just starting to become elucidated. CBG is a non-psychoactive cannabinoid found in the cannabis plant. All cannabinoids in the early stage of the cannabis plant's life begins as CBG. CBG is found in higher concentrations in hemp plants as opposed to marijuana plants, which are grown to have higher concentrations of tetrahydrocannabinol (THC). CBG has been found to act as a high affinity $\alpha_2$-adrenergic receptor agonist, a moderate affinity 5-$HT_{1A}$ receptor antagonist, and a low affinity $CB_1$ receptor antagonist. It binds with the $CB_2$ receptor, but it is currently unknown whether it acts as an agonist or antagonist.

Growing evidence indicates that endocannabinoid signaling (through the endocannabinoid system (ECS) plays a key role in the skin's regulation of biological processes. For example, in most cutaneous cell types ECS elements like metabolic enzymes and cannabinoid receptor type 1 (CB1) and cannabinoid receptor type 2 (CB2) were identified and found to play significant roles in skin inflammation, e.g. CB1 activation was shown to keep mast cell function under control, and CB1 agonists can prevent "pro-inflammatory" degranulation of mast cells. The overall conclusion of current evidence is as follows: (1) Many skin functions such as immune response, proliferation, differentiation and cell survival are at least partly regulated by ECS; (2) CB1a and CB2 receptors expressed by various skin cells are key regulators of endocannabinoid's (eCBs) effect, Suppression of cutaneous inflammation is the strongest function of ECS; and (3) CB1a and CB2 receptors expressed by various skin cells are key regulators of endocannabinoid's (eCBs) effects.

Psoriasis is a long-lasting autoimmune disease which is characterized by patches of abnormal, inflamed skin. These skin patches are typically red, itchy, and scaly. They may vary in severity from small and localized to complete body coverage. Injury to the skin can trigger psoriatic skin changes at that spot, which is known as the Koebner phenomenon.

Psoriasis is generally thought to be a genetic disease which is triggered by environmental factors. The disease affects 2-4% of the population and may begin at any age but usually starts in adulthood. There is no cure for psoriasis.

Two major immune system genes under investigation for psoriasis linkage are interleukin-12 subunit beta (IL12B) on chromosome 5q, which expresses interleukin-12B; and IL23R on chromosome 1p, which expresses the interleukin-23 receptor, and is involved in T cell differentiation. Interleukin-23 receptor and IL12B have both been strongly linked with psoriasis.

T cells are involved in the inflammatory process that leads to psoriasis. These genes are on the pathway that upregulate tumor necrosis factor-α and nuclear factor κB; two genes involved in inflammation. Recently, the first gene directly linked to psoriasis has been identified. A rare mutation in the gene encoding for the CARD14 protein plus an environmental trigger was sufficient to cause plaque psoriasis (the most common form of psoriasis).

Psoriasis is known to be associated with an up-regulation of Th1 & Th17 cytokines and a relative down-regulation of Th2 and T-regulatory (T-reg) cytokines.

ABBREVIATIONS

CB1: Cannabinoid receptors type 1
CB2: Cannabinoid receptors type 2
CBC: Cannabichromene
CBD: Cannabidiol
CBDV: Cannabidivarin
CBG: Cannabigerol
CBN: Cannabinol
ECB: Endocannabinoid
THC: Tetrahydrocannabinol
THCV: Tetrahydrocannabivarin

SUMMARY

The present invention provides a method to treat psoriasis using topical compositions containing cannabinoids, in particular cannabidiol and cannabigerol. Cannabinoids are present at 3% to 20% by weight of the total composition. The composition may be gel, liquid, spray, powder, or ointment form. Cannabinoids may be sourced naturally or synthetically and may be nano-encapsulated or micro-encapsulated. Application of topical composition may be twice daily for about six (6) weeks.

There is provided a method to treat psoriasis, the method comprises administering a topical composition containing cannabinoids onto skin areas of a subject in need thereof.

There is provided a method to treat psoriasis as above, wherein the cannabinoids are cannabidiol and cannabigerol at a total weight percent of 3% to 20% of the composition.

There is provided a method to treat psoriasis as above, wherein the cannabigerol is present at a twice to three times the weight of cannabidiol.

There is provided a method to treat psoriasis as above, wherein cannabinoids in the composition are sourced naturally.

There is provided a method to treat psoriasis as above, wherein cannabinoids in the composition are synthetic.

There is provided a method to treat psoriasis as above, wherein cannabinoids in the composition are in powder form prior to incorporation into the composition.

There is provided a method to treat psoriasis as above, wherein cannabinoids in the composition are in crystalline form prior to incorporation into the composition.

There is provided a method to treat psoriasis as above, wherein cannabinoids in the composition are microencapsulated.

There is provided a method to treat psoriasis as above, wherein cannabinoids in the composition are nanoencapsulated with particle sizes of 20 to 40 nanometers.

There is provided a method to treat psoriasis as above, wherein the composition further comprises hyaluronic acid derivative.

There is provided a method to treat psoriasis as above, wherein the hyaluronic acid derivative is sodium oleyl hyaluronate.

There is provided a method to treat psoriasis as above, wherein the composition further comprises at least one of omega-3 or omega-6 fatty acids.

There is provided a method to treat psoriasis as above, wherein the composition further comprises at least one plant extracts.

There is provided a method to treat psoriasis as above, wherein the plant extracts are neem, *Curcuma longa*, rubia cardifolia, or wrightia tinctorial extract.

There is provided a method to treat psoriasis as above, wherein the composition further comprises cacao butter.

There is provided a method to treat psoriasis as above, wherein the composition is in a hydro gel form, a liquid form, a spray form, a powder form, a gel form, or an ointment form.

There is provided a method to treat psoriasis as above, wherein the topical composition is applied twice daily in six weeks onto affected skin areas on a subject having psoriasis.

DETAILED DESCRIPTION OF CERTAIN INVENTIVE EMBODIMENTS

This present invention is capable of being embodied in various forms. The description below of several embodiments is made with the understanding that the present disclosure is to be considered as an exemplification of the claimed subject matter and is not intended to limit the attached claims to the specific embodiments illustrated. The headings used throughout this disclosure are provided for convenience only and are not to be construed to limit the claims in any way. Embodiments illustrated under any heading may be combined with embodiments illustrated under any other heading.

As used herein, the verb "to comprise" in this description, claims, and other conjugations are used in its non-limiting sense to mean those items following the word are included, but items not specifically mentioned are not excluded.

Reference to an element by the indefinite article "a" or "an" does not exclude the possibility that more than one of the elements are present, unless the context clearly requires that there is one and only one of the elements. The indefinite article "a" or "an" thus usually means "at least one." Additionally, the words "a" and "an" when used in the present document in concert with the words "comprising" or "containing" denote "one or more."

The word "cannabinoid" used in this description, claims, and other conjugations is used to mean any compound that interacts with a cannabinoid receptor and other cannabinoid mimetics, including, but not limited to, certain tetrahydropyran analogs ($\Delta^9$-tetrahydrocannabinol, $\Delta^8$-tetrahydrocannabinol, 6,6,9-trimythel-3-pentyl-6H-dibenzo[b,d]pyran-1-ol, 3-(1,1-dimethylheptyl)-6,6a7,8,10,10a-hexahydro-1-1hydroxy-6,6-dimythel-9H-dibezo[b,d]pyran-9-ol, (−)-(3S,4S)-7-hydroxy-delta-6-tetrahydrocannabinol-1,1-dimethylheptyl, (+)-(3S,4S)-7-hydroxy-Δ-6-tetrahydrocannabinol, and $\Delta^8$-tetrahydrocannabinol-11-oic acid); certain piperidine analogs (e.g., (−)-(6S,6aR,9R,10aR)-5,6,6a,7,8,9,10,10a-octahydro-6-methyl-1-3-[(R)-1-methyl-4-phenylbutoxy]-1,9-phenanthridinediol 1-acetate)); certain aminoalkylindole analogs (e.g., (R)-(+)-[2,3-dihydro-5-methyl-3-(4-morpholinylm-ethyl)-pyrrolo[1,2,3,-de]-1,4-benzoxazin-6-yl]-1-naphthelenyl-methanone); certain open pyran-ring analogs (e.g., 2-[3-methyl-6-(1-methylethenyl)-2-cyclohexen-1-yl]-5-pentyl-1, 3-benzendi-ol, and 4-(1,1-dimethylheptyl)-2,3'-dihydroxy-6'-α-(3-hydroxypropyl)-1',-2',3',4',5',6'-hexahydrobiphenyl), their salts, solvates, metabolites, and metabolic precursors.

The word "cannabidiol" refers to cannabidiol and cannabidiol derivatives. As used in this application, cannabidiol is obtained from industrial hemp extract with a low amount of THC or from cannabis extract using high-CBD cannabis cultivars. Cannabidiol may also be synthetic.

The word "cannabigerol" refers to cannabigerol and cannabigerol derivatives. As used in this application, cannabigerol is derived from industrial hemp extract with a trace amount of THC or from cannabis extract. Cannabigerol may also be synthetic.

The word "psoriasis" refers to psoriasis vulgaris, also known as plaque psoriasis, typically present as red patches on skin with white scales on top.

The table below shows the primary cannabinoids in this invention, their abbreviations, and their chemical structures.

TABLE 1

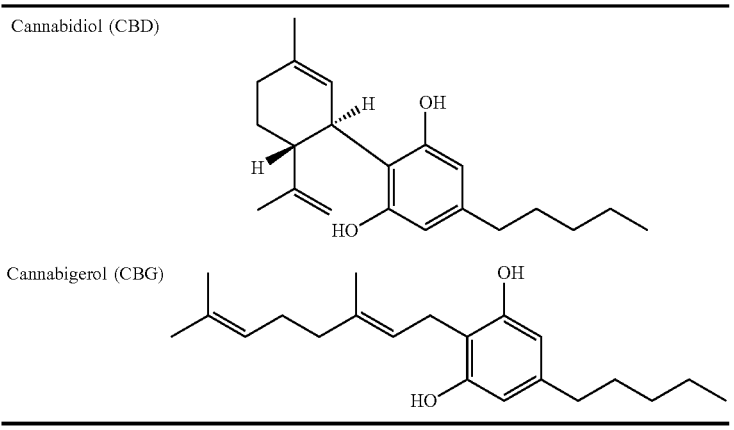

Embodiments of this application relate to methods to treat a skin condition caused by inappropriate immune system response, namely psoriasis. The methods presented concern using topical compositions containing cannabinoids, in particular; cannabidiol (CBD) and cannabigerol (CBG), as primary cannabinoids used in these methods.

In embodiments, the medicament used for this method of treatment may be a topical composition such as an oil, an ointment, a cream, or a powder containing cannabinoids, namely CBD and CBG, while other cannabinoids may be present. Cannabinoid oil may be from cannabis or hemp extraction and concentrated to reach desired cannabinoid concentrations. Cannabinoid acids may be decarboxylated during preparation to turn cannabinoid-acids into cannabinoids. After extraction from cannabis or hemp plant materials, cannabinoid extraction may be blended with other vegetable oils, such as hemp seed oil, sesame oil, coconut oil, among other suitable oils, to achieve desired concentration and/or viscosity. Blended vegetable oils containing cannabinoids may also be used to formulate other topical compositions.

In embodiments, cannabinoid extraction may be produced from cannabis or hemp plant with a certain ratio of cannabidiol and cannabigerol naturally occurring in such plants, then blended with vegetable oil, such as hemp seed oil, to give a cannabinoid oil with desired concentrations of cannabidiol and cannabigerol to be used in this invention.

In embodiments, cannabinoid topical compositions for use in this invention may be prepared by preparing separate cannabinoid oils or solutions with different primary cannabinoids before the various cannabinoid oils or solutions may be combined to give the final cannabinoid topical composition. For example, CBD-rich oil may be prepared at a certain concentration and CBG-rich oil may be prepared at a certain concentration separately. The oil may then be blended together to achieve desired cannabinoid concentrations and used in topical application. The oils may also be incorporated into a cannabinoid topical composition with other ingredients. The oils may also be blended together before being incorporated into a topical composition.

In embodiments, CBG may be present at about twice to three times the amount of CBD by weight in this topical composition. Other weight ratios between CBG and CBD in this cannabinoid oil are contemplated.

In embodiments, cannabinoid compositions used in this method may contain CBD/CBG oil at 3%-20% by weight of the total composition. The percentages given include both cannabinoids, for example the total weight percentage of CBD and CBG in the composition is 15%, as used in the experiment described below. CBG may be present at twice to three times the amount of CBD in the same composition, even though other weight ratios between CBG and CBD are contemplated. Other cannabinoids may be present at lower concentrations, such as lower than 2% or 1% by weight of the total composition. It is contemplated that CBD/CBG composition at 3%-20% by weight percent of the total composition may be used in this treatment method according to embodiments. Preferably, CBD/CBG concentration in the topical composition use comprises more than 10% by weight of the composition.

Alternatively, cannabinoids may also be incorporated into topical compositions from crystalline and/or powder form. Cannabinoids used in these embodiments must be of a high purity, such as 99% purity, but could be lower or higher. Cannabinoid concentrations in the topical compositions used in this invention may be at 0.5%-20% by weight of the total composition.

Crystalline cannabinoids may be isolated from cannabis extraction. Cannabis extraction is crystallized with C5-C12 alkane, then filtrated and vacuum dried to produce cannabinoid crystal at high purity. Crystalline cannabinoids may then be combined with vegetable oil such as hemp seed oil and used as medicament for topical application.

In embodiments, the medicament may also be a composition containing cannabinoids with additional components formulated into a composition for topical application. The cannabinoids in the composition may be nanoencapsulated and the size of the particles is between 20 and 40 nanometers (nm). The cannabinoids in these compositions may also be microencapsulated. Cannabinoids may be sourced naturally or synthetically.

In embodiments, the composition used in this method may further comprised hyaluronic acid (HA) derivatives. HA derivatives may include but is not limited to sodium oleyl hyaluronate, sodium hyaluronate, or sodium azidyl hyaluronate, among other HA derivatives. Other plant extract ingredients may be present in this composition, such as neen, *Curcuma longa*, rubia cardifolia, wrightia tinctorial extracts, among other plant extracts. The composition may further comprise cacao butter, wherein cannabinoids are incorporated into cacao butter prior to being synthesized into the composition. Other components in this composition according to embodiments may include omega-3 and/or omega-6 fatty acids. Cannabinoids may be combined with omega-3 and/or omega-6 fatty acid.

The composition may further comprise other ingredients to effectuate the form in which the composition may be prior to usage. The composition may be prepared into a cream, an ointment, a gel, a hydro gel, a spray, a powder, or other composition form suitable for topical application. Preparation of the topical compositions containing cannabinoids according to embodiments may be by methods commonly known in the art.

STUDY DESIGN

Two (2) subjects with present psoriasis who had received no therapy for at least six (6) weeks prior to the study were selected. Each subject received treatment according to embodiments of this invention. The study was conducted on lesions present on the subjects' arms. Control was by means of lesions of similar size and severity on the subjects' other arms.

Cannabinoid oil used in this study was CBD/CBG oil at 3% by weight (total weight percentage of CBD and CBG in the oil was 3%) and CBD/CBG oil at 15% by weight (total weight percentage of CBD and CBG in the oil was 15%). CBD/CBG oil was supplied as a hemp seed oil ointment containing CBD and CBG from *Cannabis sativa* L. extract. The percentages given included both cannabinoids, such that the total weight percentage of CBD/CBG in the oil was 3% or 15%. Other cannabinoids may be present at lower concentration, such as lower than 1% by weight.

Each subject was evaluated for present skin lesions due to psoriasis to choose lesions for this study. On the left arm of each subject, two skin lesions at least twenty (20) centimeters away from each other were selected for treatment. Two (2) corresponding skin lesions on the right arm were selected for control.

Each lesion was assessed with an adapted version of the severity scoring of Psoriasis Area Severity Index (PASI). The following symptoms were scored: erythema (redness), desquamation (scaling infiltration), induration (thickness), excoriations (scratch marks), lichenification (skin thickening). Each score was graded as follows: none=0, mild=1, moderate=2, severe=3.

The study was conducted by topical application of CBD/CBG oil to lesions present on the subject's skin twice daily for six weeks. CBD/CBG oil may be applied as a thin layer on the subject's skin. One lesion on the left arm received topical application of CBD/CBG oil at 15% by weight of the total composition, the other lesion of the left arm received topical application of CBD/CBG oil at 3% by weight of the total composition. In these oils, CBG are present at twice the amount of CBD by weight. Two lesions on the right arm were selected and receive placebo (0% CBD/CBG oil) to serve as controls.

PREPARATION OF CBD/CBG OIL

*Cannabis sativa* L. plants are grown, harvested, and processed to produce a botanical extract with naturally occurring cannabinoids. This botanical extract is analyzed for cannabinoid content to ascertain the weight percentage of major cannabinoids, namely CBD and CBG. The botanical extract is then blended with hemp seed oil to give CBD/CBG oil ointment.

Two CBD/CBG oil types with different CBD/CBG concentrations were prepared. The first CBD/CBG oil had CBD and CBG, in combination, at 3% by weight of the total composition. The second CBD/CBG oil had CBD and CBG, in combination, at 15% by weight of the total composition. The ratio of CBG:CBD is 2:1 in each of these oil preparations.

A third oil comprised only hemp seed oil and contained no CBD, CBG, or other cannabinoids. This third oil served as placebo in this experiment.

CBG/CBD oil was supplied by Axim Biotechnologies, Inc. The CBG/CBD strains were obtained from the company Ecohemp SRL.

DRUG TREATMENT PROCEDURE AND ADMINISTRATION

Subjects received treatment twice daily for six (6) weeks as follows:

Each subject received topical application of a thin layer of 3% CBG/CBD oil on the upper lesion and 15% CBG/CBD oil on the lower lesion of the left arm and placebo (0% CBG/CBD oil) on the two lesions of the right arm. The treatment was given twice daily.

Scoring of the lesions was by an adapted version of Psoriasis Area Severity Index (PASI), which is Table 1 as follows:

TABLE 2

| Symptom | Grading |
|---|---|
| Erythemda (redness) | |
| Desquamation (scaling) | |
| Infiltration, induration (thickness) | |
| Excoriations (scratch marks) | |
| Lichenification (skin thickening) | |

Grading was given by score from 0-3. Each score was graded as follows: none=0, mild=1, moderate=2, severe=3.

At the endpoint of the study, results were the difference as percentage of improvement between the left and right corresponding lesions. Lesions on the right arms receiving placebo were control samples. The following was the result of the study as described herein.

TABLE 3

| Condition | Subject | % Improvement of 3% CBD/CBG oil | % Improvement of 15% CBD/CBG oil |
|---|---|---|---|
| Psoriasis vulgaris | Subject 1 | 0 | 16 |
| Psoriasis vulgaris | Subject 2 | 0 | 33 |

DISCUSSION

Treatment by 3% CBG/CBD oil treatment showed no improvement on the lesions. The 15% CBG/CBD oil treatment showed 16% improvement on Subject 1 and 33% improvement on Subject 2 with psoriasis vulgaris. The improvement was intra-specimen, where the subjects' other lesions served as their own controls.

Due to the systemic penetration of the active ingredients (CBG/CBD), an overall improvement may have occurred for both the studied lesions receiving CBD/CBG oil at 3% and 15% by weight of the composition. This may have negatively influenced the perceived effectiveness of the treatment, since CBD/CBG at a lower dose may not have penetrated the skin very well. CBG was dosed twice as much as CBD, and as such might counteract some unintended actions of CBD, just like CBD is thought to counteract the cognitive impairment caused by tetrahydrocannabinol (THC).

Activation of peripheral CB1 receptors contributes to hemorrhagic and endotoxin-induced hypotension. Both CBG and CBD act as CB1 antagonists, which might suggest a possible mechanism that explains a reduction in redness in skin lesions through reduction of vasodilation. This is supported by the finding that cannabinoids can inhibit inflammatory cytokines and angiogenic growth factors such as hypoxia inducible factor-1 α (HIF-1 α), vascular endothelial growth factor (VEGF), matrix metalo-proteinases (MMPs), basic fibroblast growth factor (bFGF), Angiopoietin-2, interleukin-8 (IL-8), IL-17, and IL-2 as well as cellular adhesion molecule 1 (ICAM-1) and vascular cell adhesion molecule-1 (VCAM-1) both in vivo and in vitro. Contrary to these findings it seems that CBD induced CB1 activation causes endothelium-dependent vasorelaxation of human mesenteric arteries.

Psoriasis is known to be associated with an up-regulation of Th1 & Th17 cytokines and a relative down-regulation of Th2 and T-regulatory (T-reg) cytokines. CBD has shown to be able to shift the Th1/Th2 balance to Th2. The mechanisms of action of CBG differ from CBD but might ultimately have a Th1 suppressing effect considering its observed anti-inflammatory action in experimental inflammatory bowel disease and Huntington's disease.

The results from this study indicate a possible Th1/Th2 rebalancing mechanism. Despite the fact that only two concentrations have been used, there seems to be a clear dose-response effect, whereby higher doses (15% CBD/CBG oil) are effective where lower doses (3% CBD/CBG oil) do not show any effect. Factors influencing the dose effect might be a limited sufficient skin penetration, since skin penetration of cannabinoids may be poor.

The results present evidence for a possible synergistic role of CBD and CBG in dermatological conditions such as psoriasis. Restoring the Th1/Th2 balance is thought to be the key mechanism of action, with a possible additional direct inhibiting effect of CBG on hyper proliferation of skin cells.

CONCLUSION

These data indicate that CBG/CBD oil significantly reduces the symptoms of psoriasis. The controls receiving placebo oil did not show any improvement while CBG/CBD at higher concentration showed an improvement on psoriasis as assessed by the Psoriasis Area Severity Index.

REFERENCES

Ando T, Xiao W, Gao P, Namiranian S, Matsumoto K, Tomimori Y, et al. *Critical Role for Mast Cell Stat5 Activity in Skin Inflammation*. Cell Reports. 6 (2):366-76.

Biro T, Toth B I, Hasko G, Paus R, Pacher P. *The Endocannabinoid System of The Skin in Health and Disease: Novel Perspectives and Therapeutic Opportunities*. Trends in Pharmacological Sciences. 2009; 30 (8):411-20.

Borrelli F, Fasolino I, Romano B, Capasso R, Maiello F, Coppola D, et al. *Beneficial Effect of the Non-Psychotropic Plant Cannabinoid Cannabigerol on Experimental Inflammatory Bowel Disease*. Biochemical Pharmacology. 2013; 85 (9):1306-16.

Borrelli F, Pagano E, Romano B, Panzera S, Maiello F, Coppola D, et al. *Colon Carcinogenesis is Inhibited by The TRPM8 Antagonist Cannabigerol, a Cannabis-Derived Non-Psychotropic Cannabinoid*. Carcinogenesis. 2014; 35 (12):2787-97.

Brenneisen R, Egli A, Elsohly M A, Henn V, Spiess Y. *The Effect of Orally and Rectally Administered Delta 9-Tetrahydrocannabinol on Spasticity: a Pilot Study With 2 Patients*. International Journal of Clinical Pharmacology and Therapeutics. 1996; 34 (10):446-52.

Campos A C, Moreira F, Gomes F V, Del Bel E A, Guimarães F S. *Multiple Mechanisms Involved in the Large-Spectrum Therapeutic Potential of Cannabidiol in Psychiatric Disorders*. Philosophical Transactions of the Royal Society of London Series B, Biological Sciences. 2012; 367 (1607):3364-78.

Cascio M, Gauson L, Stevenson L, Ross R, Pertwee R. *Evidence that the Plant Cannabinoid Cannabigerol is a Highly Potent A(2)-Adrenoceptor Agonist and Moderately Potent 5HT(1A) Receptor Antagonist*. Br. J. Pharmacol. 2010; 159 (1):129-41.

Cheng Y, Hitchcock S A. *Targeting Cannabinoid Agonists for Inflammatory and Neuropathic Pain*. Expert Opinion on Investigational Drugs. 2007; 16 (7):951-65.

Cuba L F, Salum F G, Cherubini K, Figueiredo M A. *Cannabidiol: An Alternative Therapeutic Agent for Oral Mucositis?* Journal of Clinical Pharmacy and Therapeutics. 2017.

Guttman-Yassky E, Krueger J G, Lebwohl M G. *Systemic Immune Mechanisms in Atopic Dermatitis and Psoriasis with Implications for Treatment*. Experimental Dermatology. 2017.

Indhumathi S, Rajappa M, Chandrashekar L, Ananthanarayanan P H, Thappa D M, Negi V S. *T Helper-2 Cytokine/Regulatory T-Cell Gene Polymorphisms and Their Relation With Risk of Psoriasis in a South Indian Tamil Cohort*. Human immunology. 2017; 78 (2):209-15.

Iseger T A, Bossong M G. *A Systematic Review of The Antipsychotic Properties of Cannabidiol in Humans*. Schizophrenia Research. 2015; 162 (1-3):153-61.

Jäger A, Dardalhon V, Sobel R A, Bettelli E, Kuchroo V K. *Th1, Th17 and Th9 Effector Cells Induce Experimental Autoimmune Encephalomyelitis with Different Pathological Phenotypes*. Journal of Immunology (Baltimore, MD: 1950). 2009; 183 (11):7169-77.

Kinghorn A D, Falk H, Gibbons S, Kobayashi J. Phytocannabinoids: *Unraveling the Complex Chemistry and Pharmacology of Cannabis sativa*: Springer International Publishing; 2017.

Lambert D M, Fowler C J. *The Endocannabinoid System: Drug Targets, Lead Compounds, and Potential Therapeutic Applications*. J. of Medicinal Chemical. 2005; 48 (16):5059-87.

Maccarrone M, Bab I, Biro T, Cabral G A, Dey S K, Di Marzo V, et al. *Endocannabinoid Signaling at the Periphery: 50 Years After THC*. Trends in Pharmacological Sciences. 2015; 36 (5):277-96.

McGilveray I J. *Pharmacokinetics of Cannabinoids*. Pain Research & Management. 2005; 10 Suppl A:15a-22a.

Mashiko S, Bouguermouh S, Rubio M, Baba N, Bissonnette R, Sarfati M. *Human Mast Cells Are Major Il-22 Producers in Patients with Psoriasis and Atopic Dermatitis*. The Journal of Allergy and Clinical Immunology. 2015; 136 (2):351-9.el.

Mechoulam R, Peters M, Murillo-Rodriguez E, Hanuš L O. *Cannabidiol—Recent Advances*. Chemistry & Biodiversity. 2007; 4 (8):1678-92.

NIAMS. *Questions and Answers about Psoriasis*: National Institute of Arthritis and Musculoskeletal and Skin Diseases (NIAMS); 2016 [updated July 2016. Available from: https://www.niams.nih.gov.health_info/psoriasis/#5.

Norooznezhad A H, Norooznezhad F. *Cannabinoids: Possible Agents for Treatment of Psoriasis via Suppression of Angiogenesis and Inflammation*. Med. Hypotheses. 2017; 99:15-8.

Pinton P C. *Psoriasis Differential Diagnosis*. Clinical Dermatology. 2013; April-June; 2 (2):60-6.

Raphael I, Nalawade S, Eagar T N, Forsthuber T G. *T Cell Subsets and Their Signature Cytokines in Autoimmune and Inflammatory Diseases*. Cytokine. 2015; 74 (1):5-17.

Russo E B, Burnett A, Hall B, Parker K K. *Agonistic Properties of Cannabidiol at 5-HT1a Receptors*. Neurochemical Research. 2005; 30 (8):1037-43.

Ryberg E, Larsson N, Sjögren S, Hjorth S, Hermansson N, Leonova J, et al. *The Orphan Receptor GPR55 is a Novel Cannabinoid Receptor*. Br. J. Pharmacol. 2007; 152 (7): 1092-101.

Small-Howard A L, Shimoda L M, Adra C N, Turner H. *Anti-Inflammatory Potential of CB1-Mediated Camp Elevation in Mast Cells*. The Biochemical Journal. 2005; 388 (Pt 2):465-73.

Sugawara K, Biro T, Tsuruta D, Toth B I, Kromminga A, Zakany N, et al. *Endocannabinoids Limit Excessive Mast Cell Maturation and Activation in Human Skin*. The Journal of Allergy and Clinical Immunology. 2012; 129 (3):726-38.e8.

Toh M R, Teo V, Kwan Y H, Raaj S, Tan S Y, Tan J Z. *Association Between Number of Doses Per Day, Number of Medications and Patient's Non-Compliance, and Frequency of Readmissions in a Multi-Ethnic Asian Population*. Preventive Medicine Reports. 2014; 1:43-7.

Turcotte C, Blanchet M R, Laviolette M, Flamand N. *The CB2 Receptor and Its Role as a Regulator of Inflammation*. Cellular and Molecular Life Sciences: CMLS. 2016; 73 (23):4449-70.

Valdeolivas S, Navarrete C, Cantarero I, Bellido M L, Munoz E, Sagredo O. *Neuroprotective Properties of Cannabigerol In Huntington's Disease: Studies In R6/2 Mice and 3-Nitropropionate-Lesioned Mice*. Neurotherapeutics: The Journal of the American Society for Experimental NeuroTherapeutics. 2015; 12 (1):185-99.

Weiss L, Zeira M, Reich S, Har-Noy M, Mechoulam R, Slavin S, et al. *Cannabidiol Lowers Incidence of Diabetes in Non-Obese Diabetic Mice*. Autoimmunity. 2006; 39 (2): 143-51.

WHO. *Global Report on Psoriasis*. World Health Organisation; 2016. p. 49.

All references, including publications, patent applications, and patents cited herein are hereby incorporated by reference to the same extent as if each reference were individually and specifically indicated to be incorporated by reference and were set forth in its entirety herein.

It will be readily apparent to those skilled in the art that a number of modifications and changes may be made without departing from the spirit and the scope of the present invention. It is to be understood that any ranges, ratios, and range of ratios that can be derived from any of the data disclosed herein represent further embodiments of the present disclosure and are included as part of the disclosure as though they were explicitly set forth. This includes ranges that can be formed that do or do not include a finite upper and/or lower boundary. Accordingly, a person of ordinary skill in the art will appreciate that such values are unambiguously derivative from the data presented herein.

What is claimed is:

1. A method to treat psoriasis, the method comprising:
    administering a topical composition containing cannabinoids onto skin areas affected by psoriasis of a subject in need thereof,
    wherein the topical composition comprises cannabidiol (CBD) and cannabigerol (CBG) at a total weight percent of 15% of the composition,
    wherein the topical composition comprises CBG and CBD in a weight ratio of 2:1 (CBG: CBD), and
    wherein the topical composition is an ointment.

2. The method of claim 1, wherein the cannabinoids in the composition are sourced naturally.

3. The method of claim 1, wherein the cannabinoids in the composition are synthetic.

4. The method of claim 1, wherein the cannabinoids in the composition are nanoencapsulated with particle sizes of 20 to 40 nanometers.

5. The method of claim 1, wherein the composition further comprises-sodium oleyl hyaluronate.

6. The method of claim 1, wherein the topical composition is applied twice daily per day for six weeks onto affected skin areas on a subject having psoriasis.

* * * * *